(12) United States Patent
Rajendran et al.

(10) Patent No.: US 8,759,547 B2
(45) Date of Patent: Jun. 24, 2014

(54) EXTRACTION OF VITAMIN E FROM PLANT MATTER

(76) Inventors: Ramaswamy Rajendran, Bangalore (IN); Kamala Rajendran, Bangalore (IN)

(*) Notice: Subject to any disclaimer, the term of this patent is extended or adjusted under 35 U.S.C. 154(b) by 0 days.

(21) Appl. No.: 13/824,283

(22) PCT Filed: Jul. 30, 2012

(86) PCT No.: PCT/IN2012/000529
§ 371 (c)(1),
(2), (4) Date: Mar. 15, 2013

(87) PCT Pub. No.: WO2013/018104
PCT Pub. Date: Feb. 7, 2013

(65) Prior Publication Data
US 2013/0178519 A1  Jul. 11, 2013

(30) Foreign Application Priority Data
Aug. 4, 2011  (IN) ............................. 2679/CHE/2011

(51) Int. Cl.
*C07D 311/72*  (2006.01)
(52) U.S. Cl.
USPC ........................... 549/401; 549/413; 514/458

(58) Field of Classification Search
USPC .................................. 549/401, 413; 514/458
See application file for complete search history.

(56) References Cited

U.S. PATENT DOCUMENTS

| | | |
|---|---|---|
| 5,157,132 A | 10/1992 | Tan et al. |
| 6,124,268 A | 9/2000 | Ghosal |
| 6,350,453 B1 | 2/2002 | Tan et al. |
| 2009/0041870 A1 | 2/2009 | Tan et al. |

OTHER PUBLICATIONS

Meena, Ak et al., Evaluation of Physicochemical and Preliminary Phytochemical Studies on the Fruit of Emblica Officinalis Geartn, Asian Journal of Pharmaceutical and Clinical Research, 2010, vol. 3, No. 3, pp. 242-243.

*Primary Examiner* — Kortney L Klinkel
*Assistant Examiner* — John Mauro
(74) *Attorney, Agent, or Firm* — Robert E. Bushnell, Esq.

(57) ABSTRACT

A process for the extraction of Vitamin E from annatto plant matter is disclosed wherein annatto seed matter is subjected, before extraction, to acidification using amla fruit matter. After the acidification, the mixture of the two plant matters is extracted by water. The acidification converts the vitamin E compounds in the plant matter into more water-soluble forms, thus enhancing the vitamin yield. More of the vitamin is obtained in the ester form than in the form of vitamin alcohols. Processing time is reduced.

30 Claims, No Drawings

EXTRACTION OF VITAMIN E FROM PLANT MATTER

CLAIM OF PRIORITY

This application makes reference to, incorporates the same herein, and claims all benefits accruing under 35 U.S.C. §365 (c) of my PCT International application entitled EXTRACTION OF VITAMIN E FROM PLANT MATTER filed on 30 Jul. 2012 and duly assigned Serial No. PCT/IN2012/000529. This application is a submission to enter the national stage under 35 U.S.C. §371. Furthermore, this application makes reference to, incorporates the same herein, and claims all benefits accruing under 35 U.S.C. §119 from applications filed in the Indian Intellectual Property Office on 4 Aug. 2011 and there duly assigned Serial No. 2679/CHE/2011.

BACKGROUND OF THE INVENTION

1. Field of the Invention

This invention relates to a process for extracting vitamins from plant matter and more particularly to a process of extracting vitamin E from Annatto plant matter.

2. Description of the Related Art

Vitamin E refers to a group of fat-soluble compounds that are found in plants and plant-derived matter such as, for example, vegetable oils. It is also found in some oils/fats of animal origin. Vitamin E appears to have multiple roles in human metabolism. The main biological activity of vitamin E is understood to be as a powerful antioxidant. It is also reported to reduce free radicals and inhibit the production of reactive oxygen species (ROS). Compounds of the vitamin E group play a role in the immune system, in the regulation of gene expression, in the regulation of some enzymatic activities, as an anti-carcinogenic and in other functions.

Said group comprises four tocopherol and four tocotrienol compounds which are identified by the prefixes alpha, beta, gamma and delta. Wheat germ oil, sunflower seeds and oil, safflower seeds and oil, palm oil, fish oils, soyabean seeds and oil, annatto seeds and almonds are some of the sources rich in these compounds. Some of the said sources are rich in the tocotrienols while the others contain more of the tocopherols.

The vitamin in these sources is mostly in the form of esters that are referred to herein collectively as vitamin esters. A small quantity of the vitamin is found in the form of alcohols which is referred to herein collectively as vitamin alcohols.

A generalised process for the recovery of fat-soluble vitamins (such as vitamin E) found dissolved in natural vegetable oils comprises saponifying the oil. During saponification the oil gets converted to a soap while some of the vitamin esters get converted to vitamin alcohols.

The vitamin esters and alcohols and some other compounds such as phytosterols and squalene in the oil separate out being immiscible in the soap layer. This layer is separated from the soap and is referred to herein as the semi-concentrate.

In addition to vitamin E esters and alcohols, said semi-concentrate contains esters and alcohols of other oil-soluble vitamins such as A and D. Through a process of solution partitioning the vitamin E component is isolated, purified and formulated into capsules or other forms. Before formulation, it may be dissolved in some suitable bland oil such as for example, corn oil and the solution packaged. The semi-concentrate may be concentrated and the concentrate packaged into appropriate doses.

In a variant of the above process, the concentrate is esterified. The vitamin alcohols get converted to the ester form which is then separated.

In another prior art process the original vitamin containing oil is subjected to high vacuum distillation to distill off the vitamin in the ester form. The vitamin ester distillate is subjected to purification steps and then packaged.

U.S. Pat. No. 2,380,409, to L. O. Buxton, discloses a process wherein a marine oil is contacted with a liquid aliphatic organic solvent at an elevated temperature. The extract is cooled to a low temperature at which the solution of the vitamin esters and alcohols in the solvent separates out. This solution is also referred to as the semi-concentrate. The solvent is removed from the semi-concentrate which is then contacted with a highly polar solvent that is substantially immiscible with the semi-concentrate at low temperatures.

The solution containing the polar solvent and the said esters and alcohols is cooled. The polar solvent phase containing the vitamin alcohols separates out. The non-solvent layer is the ester concentrate and contains the natural vitamin esters originally present in the oil. It is stated to be substantially free of free-fatty acids and the disagreeable odour and colouring components present in the oil. In a variant, the marine oil is directly treated with the polar solvent and the residual oil treated with the said aliphatic organic solvent to obtain the vitamin esters.

U.S. Pat. No. 7,575,767 B2, to C. Y. May, discloses a process wherein palm oil is treated with a low alkyl alcohol. An acid or alkaline catalyst is provided, which causes esterification and trans-esterification of the vitamin alcohols and esters. The vitamin alcohols get converted to esters and a part of the vitamin esters originally present in the oil gets trans-esterified. The esterified mass is subjected to three stages of short path vacuum distillation to give a vitamin E enriched fraction, a fraction containing the phytosterols and one containing squalene.

A similar process wherein triple distillation is adopted has been reported for extraction of vitamin E, squalene and sterols from condensates obtained during vegetable oil refining and/or the distillates obtained during the deodorisation of plant oils. The process employs bioethanol, glycerol and hydrocarbons generated in the process and does not require any external solvent of petroleum or other origin.

Processes using extraction by several different solvents such as 96% ethanol and hexane, petroleum ether, ethyl acetate, methanol and NaOH and EDTA, n-hexane and others have been reported. In one process, the solvent extraction is assisted by ultrasound inputs.

Super critical extraction with carbon-dioxide is also practised in the prior art. Other methods based on chromatography, enzyme catalysis etc are also known.

The drawbacks in the solvent extraction processes of prior art reported above are:
  (i) The presence of vitamin alcohols in the vitamin product. Vitamin alcohols make the product unstable and reduce the shelf life. In some processes the product is mostly all in the form vitamin alcohols with very little of the original natural vitamin esters.
  (ii) In some processes, synthetic vitamin esters are produced which come into the product. Such synthetic esters appear to have lesser efficacy than the natural vitamin esters contained in vitamin E containing oils.
  (iii) Where vitamin alcohols are present in the product, the disagreeable odour factors in the oil come out into product along with the vitamin alcohols. Similarly, disagreeable taste and colouring factors also come out in the product extract.

(iv) The employment of solvents of petroleum origin.
(v) In the processes employing esterification and transesterification operations, the said operations are not complete and some vitamin alcohols tend to remain unconverted.

SUMMARY OF THE INVENTION

The above drawbacks are removed in the process of the invention for making vitamin E from plant matter.
  (i) The problem of residual vitamin alcohols in the vitamin product is substantially eliminated in the process of the invention through the acidification of the plant matter to be extracted. Said acidification is by means of the addition of a second plant matter that comprises one or more acidic components. The acidification ensures that substantially all the vitamin alcohol matter is converted into ester form.
  (ii) As the esterification is by means of naturally-occurring plant-based acids, there is substantially no production of synthetic esters and no loss in efficacy.
  (iii) Solvents of petroleum origin are totally avoided in the process of the invention wherein water is used as the solvent.
  (iv) Because of the substantial absence of vitamin alcohols in the vitamin E product of the invention, problems of undesirable odours, taste and discolouration are substantially absent.

In addition to removing the above drawbacks, the process of the invention offers the following advantages:
  (i) a vitamin E product of greater efficacy and one that is more assimilable;
  (ii) the use of a low cost solvent such as water;
  (iii) the extract product of the invention is substantially in dosage form and easily converted into any of the other known dosage forms;
  (iv) the extract product of the invention is a suitable intermediate for easy conversion into other pharmaceutical forms such as any of the known pharmaceutical salts or carried on any of the known pharmaceutical carriers;
  (v) the extract product of the invention is a suitable intermediate for any of the downstream processes such enhancing activity and efficacy; topping-up operations; addition of other vitamins, minerals and other nutrients; incorporation of additives for colour, texture, bulk, flavour, odour and others; conversion into food, pharmaceutical and nutraceutical compositions;
  (vi) minimising/substantially preventing the presence of said vitamin alcohols in the extract product;
  (vii) cost savings through the elimination of solvent handling and recovery systems; and
  (viii) a higher extraction efficiency and better yield of the vitamin E product.

The present invention includes a process for extracting vitamin E from annatto plant matter, the process including the steps of providing annatto plant matter, converting the plant matter of the providing annatto step into a form having increased contact area, providing amla plant matter, converting the plant matter of the providing amla step into a form having increased contact area, mixing the annatto form having increased contact area with the amla form having increased contact area, extracting the mixture formed in the mixing step with one of water and dilute aqueous plant extract at a predetermined temperature and for a predetermined period of time to obtain a first extract and spent plant matter, concentrating the first extract, and drying the first extract to yield a vitamin E product. Water or dilute aqueous plant extract serves as the sole solvent utilized in the extraction process.

Those skilled in the art will appreciate that the form of the annatto plant matter having increased contact area may be a pulp and that the spent plant matter (plant matter after extraction) may be successively extracted to obtain a plurality of extracts. The successively obtained extracts may be combined with the first extract prior to concentration, may be concentrated individually, or may be used as the extraction solvent in the extraction of a freshly prepared batch of combined and prepared annatto and amla plant matters.

In certain embodiments, the process for extracting vitamin E from annatto plant matter may include both annatto and amla pulp matters being contacted for a length of time before being subjected to the extracting step, the contacting being promoted by an intermixing process.

In additional embodiments, the process for extracting vitamin E from annatto plant matter may include the further processing of the vitamin E product according to at least one of the steps of conversion of the vitamin E product into a pharmaceutically acceptable salt, dissolution of the vitamin E product in a suitable solvent to give a liquid form of the product, conversion of the vitamin E product into an adduct of the vitamin E product with a pharmaceutically acceptable carrier, conversion of the vitamin E product into a dosage form, conversion of the vitamin E product into a form offering at least one of improved efficacy and improved assimilability, conversion of the vitamin E product by adsorbing the extract having one of a solid form, a semi-solid form and a liquid form on a suitable excipient, topping-up of any constituent of the product extract, addition of new constituents to the product extract, conversion of the vitamin E extract into one of a food formulation, a nutraceutical formulation, and a medicinal formulation, finishing of the vitamin E product by a processing operation comprising at least one of crushing, grinding, milling, sifting, mixing and homogenising, and incorporation of additives for improvement of at least one of color, texture, taste, bulk, flavour, odor and preservation.

In certain embodiments of the process for extracting vitamin E from annatto plant matter, at least one additional material is coextracted, and the at least one additional material comprises at least one of a vitamin, a mineral, a constituent present in the annatto seed matter, and a constituent present in the amla fruit matter.

In certain embodiments of the process for extracting vitamin E from annatto plant matter, at least one of the annatto plant matter and the amla plant matter is subjected to at least one of cutting, chopping, dicing, crushing, grinding, pulverising, milling, screening, sifting, washing, blanching and sifting.

Other advantages will be apparent from the description and claims herein. The objects of the invention will also be apparent from the description and claims herein.

DETAILED DESCRIPTION OF THE INVENTION

The process of the invention is based on solvent extraction of the vitamin E containing oil.

The process of the invention employs a naturally occurring solvent, namely water. Attention is drawn to co-pending application for Indian Patent No. 2677/CHE/2011, dated 4 Aug. 2011, by the present inventors/applicants, which deals with the extraction of plant matters by water. The entire disclosure therein is incorporated herein by reference.

According to embodiments of the present invention, the plant matter to be extracted may be mixed with a second plant matter that may comprise one or more acidic components such as citric, tartaric, ascorbic, succinic or other acids. The mixture of the two plant matters may be contacted with water, which may act as the extraction solvent. The plant acids may then convert the water-insoluble nutrients (vitamins and minerals) found in the first plant matter into water-soluble compounds that are then easily extracted by the water solvent.

Each of said first plant matter and said second plant matter may comprise a single plant species or a mixture of plant species. This extended scope is intended to be conveyed by the terms 'first plant matter(s)' and 'second plant matter(s)' used herein. This scope is intended even where references to plant matter herein are not given in the said forms for the sake of convenience.

In embodiments of the process of the present invention, the addition of acidic components may thus serve to increase the range of extraction by the water solvent. In fact, in the process of extraction disclosed herein, substantially all the referenced nutrients may be extracted and come out into the extract, irrespective of whether said nutrients were originally water-soluble or water-insoluble. A further advantage of the disclosed process of extraction is that the application of said acidic components may considerably increase the yield of the said nutrients over that obtained by prior art processes. Not only water-insoluble nutrients may be converted into soluble forms, but some of the water-soluble nutrients may be converted into forms that are more water soluble, resulting in increased yields of the vitamin.

In the process of extraction of the present invention, the role of the added acidic components is important. Said acidic components may not only enhance the yield of the vitamin E product but also may suppress the amount of the vitamin alcohols appearing in the product. Said acidification treatment may convert much of the vitamin alcohol material into other forms.

The acidic constituents employed for the esterification of the vitamin E alcohols in processes corresponding to embodiments of the invention are naturally occurring compounds. In certain embodiments of the process of the invention, the vitamin E containing annatto seeds may be mixed with amla fruit before extraction. This mixture may then be extracted by means of water in the process of the invention. While the present inventors do not wish to be bound by any particular explanation, it will be observed that esterification of the vitamin alcohols present in the annatto seeds may be caused by the citric and tartaric acid constituents of amla fruit matter. Some have said that esterification also occurs through other routes. Without wishing to be bound by any particular theory, the present inventors believe that some increase in the vitamin yield may arise from the formation of water-soluble adducts and complexes between the different forms of the vitamin and the acidic matter. The major advantage of certain embodiments of the process of the invention, as established by the investigations of the present inventors, is that higher contents of vitamin E, as compared to prior art processes, are obtained in the extract, and this leads to considerable savings in energy and processing times, such as in the concentration operations in the process of the invention. A final product having up to about 15% by wt. of vitamin E may be obtained in the process. Another advantage of many embodiments is that the solvent and the treatment agents are naturally occurring compounds rather than synthetic.

The present inventors also observe that the use of acidic plant matter may help to rupture the plant cells. Said cell rupture may, in turn, contribute to an increase in the vitamin yield.

As the said second plant matter has been traditionally used as food and also for the medicinal value thereof, the extract product resulting from many embodiments of the processes of the present invention is non-toxic. The use of water as a solvent also may help to ensure that the extract is non-toxic.

According to certain embodiments of the invention, therefore, there is provided a process for extracting vitamin E, and optionally other nutrients and plant constituents, from annatto plant matter(s) comprising the steps of:

(i) providing annatto plant matter(s), preferably seed matter;
(ii) converting the plant matter(s) of step (i) into a form having increased contact area, such as, for example, a pulp;
(iii) providing amla plant matter(s), preferably fruit matter,
(iv) converting the plant matter(s) of step (iii) into a form having increased contact area such as, for example, a pulp;
(v) mixing the materials of steps (ii) and (iv),
(vi) extracting the said mixture of step (v) with water or a dilute extract coming from another extraction stage if any, or mixtures of such extracts, at a predetermined temperature and for a predetermined period of time to obtain a first extract and spent plant matter,
(vii) optionally successively extracting the spent plant matter of step (vi) according to step (vi) to obtain a plurality of said extracts,
(viii) individually or collectively concentrating one or more extracts of step (vi) and/or (vii) and optionally using a weak extract(s) of step (vii) as solvent for extraction in step (vi), and
(ix) drying the extract(s) from step (viii) to yield the vitamin E product.

In this process, the annatto seeds constitute said first plant matter and the amla fruits constitute said second plant matter. Within the scope of the invention, said first plant matter may comprise one or more further plant species that are sources of vitamin E or of any other desired plant principle. In addition, one or more of the plant species forming part of said first plant matter may comprise acidic component(s) that may participate in the acidification of the vitamin E forms present in the first plant matter. It will be observed that the process of the invention is easily and simply extendable to extraction of other nutrients and constituents in plant matter, in addition to vitamin E.

The said second plant matter may also comprise a plurality of plant species within the scope of the invention. Within the scope of the invention, the species in the said second plant matter may be a source of said acidic compound(s) and/or vitamin E or both. Thus, within the scope of the invention, said first and second plant matters may each play a single role of being the source of the vitamin E or of the acidic compound (s) or a dual role of being a source of both. Within the scope of the invention, both said plant matters may be sources of other desired nutrients and principles. A said species of the second plant matter may comprise one acidic compound or a plurality thereof. Higher yields are achieved when the second plant matter adopted comprises a greater number of said acidic compounds. The option of different combinations of said acidic compounds offered by the invention is an important tool in optimising the process yield and product profile and in securing cost benefits in capital and operating costs.

The process of the invention is applicable to plant matter other than annatto seeds, containing vitamin E. Within the scope of the invention, annatto plant matter may be substituted partly or fully by other suitable plant matter containing vitamin E. Any mixture of such plant matter may be extracted by the process of the invention. The amla plant matter may also be replaced by other plant matter containing one or more plant acids within the scope of the invention. The use of mixtures of such plant matters as said first and/or second plant matters is also within the scope of the invention.

Preferably, the annatto plant matter comprises annatto seeds. Within the scope of the invention, the annatto and amla plant matters may be pre-treated by any optional preparatory process or operation such as crushing, grinding, screening, mixing, drying, milling, homogenising, washing, cleaning, blanching or others as required for better and cost effective processing as would be suggestible to a person in the art. Within the scope of the invention, the said first and second plant matter(s) may comprise any plant part such as leaves, fruits, flowers, stems, bark, seeds, roots, rhizomes or others, or mixtures thereof.

Adoption of conventional operations such as filtration, separation in the interests of better and more cost-effective processing as would be suggested to a person in the art is within the scope of the invention.

For contacting the first and second plant matters, any of the known contacting processes may be adopted within the scope of the invention. Said contacting may be in the solid state or the plant matters may be contacted in slurry phase wherein they are slurried in a suitable liquid medium. Preferably, said liquid medium is water, the solvent adopted in the process of the invention. Adoption of heating, stirring, agitating, cooking and other such operations to increase the yield and reduce the processing time are within the scope of the invention. Use of pressure in the cooking operation is within the scope of the invention.

Said contacting may be individualised in that individual species of the said first and second plant matter(s) are contacted or may be collectivised in that groups of said species are contacted. Such options are useful tools for securing processing and cost benefits, in particular, increased vitamin yields.

Different methods of extraction are known in the art and any one or more thereof may be adopted in the process of the invention. The extraction operation may comprise a plurality of stages and different combinations of material flows (streams) such as of the spent matter and the extracts within the scope of the invention. The process of the invention is suited for single stage extraction or multiple stage extraction. It is also suited for batch operation or for continuous or semi-continuous operation.

Preferably the extract is spray dried. The product may be subjected to any of the known finishing operations such as crushing, grinding, milling, screening, sifting, mixing, blending, homogenising, agglomerating (pelletising, tabletting and others) for better product features within the scope of the invention. The product of the invention may be in the form of a dilute solution, or a concentrated solution or in the form of a solid or semi-solid. Within the scope of the invention, the vitamin E product of the invention may be adsorbed on suitable excipient(s). Such process modifications that would be suggested to a person in the art are within the scope of the invention.

The terms 'spent matter' and 'spent plant matter' are intended to mean the same and refer to the extracted plant matter at any stage in the extraction process such that the 'spent matter' may be fully spent or partly spent. The term 'extract' may be understood to mean the product arising at any stage in the process of the invention or in the optional steps mentioned.

References to 'enlarged surface area' are to the breaking down of the plant matter so as to encourage the reaction between the vitamin matter and the acidic compound(s) by increasing the contact area. Such enlargement of surface area may be achieved by operations such as size reduction through crushing, grinding, powdering, milling and others or by pulping, macerating, chipping, cutting, slicing and/or other similar operations. All such possible operations are within the scope of the invention.

Within the scope of the invention, said first and second plant matters may comprise any part of the one or more species forming part thereof. For example, the said annatto seed matter may be replaced by another part of the annatto plant, such as for example, leaves, fruits, flowers, roots, stems, branches and others. Use of mixtures of plant parts are also within the scope of the invention. Similarly, other parts of the amla plant may be adopted as said second plant matter. This invention has observed that adoption of annatto seeds and amla fruit matter gives higher yields of the vitamin than other combinations of plant matters.

The term 'extract', is used to refer to the process of the invention as a whole and also to the operation of extraction which forms one of the steps thereof. The meaning appropriate to the context may be taken.

As would be observed, a number of variants of the process of the invention are feasible and are within the scope of the invention. For example, changes in the order of the steps ennumerated above are feasible which would result in several such variants. Various procedures of extraction such as co-current, counter-current and hybrid and various flow arrangements of the extracts and spent matter are also feasible. All such variants are within the scope of the invention. Further variants arise by adopting different methods of extract concentration and solvent removal and by adopting different procedures for operations such as filtration, separation, centrifugation and others. All such variants are within the scope of the invention.

Example 1

In order to provide a clearer understanding of the invention, and without limitation to the scope thereof, an embodiment thereof is described hereinbelow.
(i) Fresh annatto seeds were collected, crushed in a stainless steel multimill to get seed pulp.
(ii) Fresh amla fruits were collected, crushed in a stainless steel multimill to get
(iii) amla pulp.
(iv) About 495 kgs of annatto seed pulp with about 5 kg of amla fruit pulp were charged into an extractor.
(v) The extractor comprised a stainless steel vessel of about 5000 L capacity provided with an agitator system and a surrounding jacket for heating by steam.
(vi) About 2000 L of water were charged into the extractor.
(vii) The extractor contents were maintained at about 50-65 deg C. by heating with steam.
(viii) The extraction was carried out for a period of about 6 hours.
(ix) During the extraction, the extract was recirculated across the bed containing the annatto and amla pulp mixture in the extractor.
(x) At the end of the extraction period, the extract was collected in a tank. The extract was denoted A. About 1500 L of extract was obtained.
(xi) The spent pulp was subjected to another extraction by the procedure as outlined herein. The extract was withdrawn at the end of the extraction period and collected in a tank. This extract was denoted B. About 1500 L extract was obtained.

(xii) The spent pulp after the two extractions mentioned herein was further extracted in a third extraction with about 1500 L water. The temperature was maintained at about 50-65 deg C. during extraction.
(xiii) About 1500 L extract was obtained. This extract is denoted C.
(xiv) Extracts A and B were both separately concentrated in concentrators at about 50-65 deg C. down to a volume of about 150 L each. Falling film evaporators were used. The two extracts contained the tocopherols in aqueous solution.
(xv) Extract C was used as solvent and charged into extractor for extracting said pulp mixture as mentioned herein.
(xvi) The two concentrated extracts A and B were combined, giving about 300 L of concentrated extract. This was filtered in a stainless steel Nutsche type filter using 'Hyflosupercel' as filter aid.
(xvii) The clear filtrate obtained from step (xvi) was spray dried in a stainless steel spray drier at about 170 to 180 deg C. to yield the vitamin E tocopherols in a powder form.
(xviii) The vitamin E powder was ground in a stainless steel multimill and then sifted in a stainless steel sifter to a particle size of about 40-80 mesh. The sifted material was blended in an octagonal blender for about one hour to get a homogeneous powder material. The quantity of the product (yield) was about 50 kgs.

The analysis of the vitamin E powder product is given below.

The process of the invention may be simply and easily adapted for batch, continuous or semi-continuous operation.

Embodiments and variations other than described herein above are feasible by persons skilled in the art and the same are within the scope and spirit of this invention.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

The invention claimed is:

1. A process for extracting vitamin E from annatto plant matter, the process comprising the steps of:
providing annatto plant matter;
converting the plant matter of the providing annatto step into a form having increased contact area;
providing amla plant matter;
converting the plant matter of the providing amla step into a form having increased contact area;

TABLE I

Comparison of the extract of the embodiment of the invention with the required specifications.
Certificate of Analysis

| Physical Analysis | Specification | Actual Values | Testing method |
| --- | --- | --- | --- |
| Appearance and Color | Orange brown powder | Complies | Visual |
| Identification | Positive | Complies | HPTLC |
| Odor | Characteristic | Complies | Organoleptic |
| Taste | Characteristic | Complies | Organoleptic |
| Particle size | NLT 98% thro' 20 mesh | Complies | USP XXIII |
| Loss on Drying | NMT 6% w/w | 3.1% | USP XXIII (IR) |
| Assay of Actives | Specification | Result | Test Method |
| Assay of Vitamin E | NLT 15% | 15.8% | HPLC |
| Chemical Impurities | Specification | Result | Test Method |
| Total Heavy Metals | NMT 10 ppm | Complies | USP XXIII |
| Lead | NMT 5 ppm | Less than 0.01 PPM | USP XXIII |
| Cadmium | NMT 1 ppm | Less than 0.01 PPM | USP XXIII |
| Arsenic | NMT 3 ppm | Less than 0.01 PPM | USP XXIII |
| Mercury | NMT 1 ppm | Less than 0.001 PPM | USP XXIII |
| Residual pesticides | Absent | Absent | USP XXIII |
| Microbiology | Specification | Result | Test Method |
| Total Plate Count | 1000 cfu/gram max | Complies | USP XXIII |
| Yeast and Mold | 100 cfu/g max | Complies | USP XXIII |
| E. coli | Absent | Absent | USP XXIII |
| Coliforms | Absent | Absent | USP XXIII |
| Salmonella | Absent | Absent | USP XXIII |
| Pseudomonas aeruginosa | Absent | Absent | USP XXIII |
| Staphylococcus aureus | Absent | Absent | USP XXIII |

Remarks The extract complies with the required specifications producing a mixture that is more acidic than the annatto plant matter by mixing the annatto form having increased contact area with the amla form having increased contact area;

extracting the mixture formed in the mixing step with one of water and dilute aqueous plant extract at a predetermined temperature and for a predetermined period of time to obtain a first extract and spent plant matter, the dilute aqueous extract used in the extracting step being a first extract from at least one previously conducted extracting process;

concentrating the first extract; and drying the first extract to yield a vitamin E product, water or the first extract being the sole solvent utilized in the extraction process.

2. The process for extracting vitamin E from annatto plant matter as claimed in claim 1, the annatto plant matter being derived from seed matter, the amla plant matter being derived from fruit matter, and both the annatto seed and the amla fruit matters being converted into pulps and combined in the mixing step, the mixing step producing a mixture that is more acidic than is the annatto plant matter.

3. The process for extracting vitamin E from annatto plant matter as claimed in claim 2, both said pulp matters being contacted for a length of time before being subjected to the extracting step, said contacting being promoted by an intermixing process.

4. The process for extracting vitamin E from annato plant matter as claimed in claim 1, the vitamin E product being further processed according to one or more of the following steps:
   converting the product into a pharmaceutically acceptable salt;
   dissolving the product in a suitable solvent to give a liquid form of the product;
   converting the product into an adduct of the product with a pharmaceutically acceptable carrier;
   converting the product into a dosage form;
   converting the product extract into one of a food formulation, a nutraceutical formulation and a medicinal formulation;
   finishing of the product by a processing operation comprising at least one of crushing, grinding, milling, sifting, mixing and homogenizing; and
   incorporating additives for improvement of at least one of colour, texture, taste, bulk, flavour, odour and preservation.

5. The process for extracting vitamin E from annatto plant matter as claimed in claim 1, at least one additional material being coextracted, the at least one additional material being a vitamin, a mineral, a constituent present in the annatto seed matter and/or a constituent present in the amla fruit matter.

6. The process for extracting vitamin E from annatto plant matter as claimed in claim 1, at least one of the annatto plant matter and the amla plant matter being subjected to at least one of cutting, chopping, dicing, crushing, grinding, pulverising, milling, screening, washing, blanching and sifting.

7. The process according to claim 1, the vitamin E product comprising about 12 wt % to about 15 wt % of vitamin E.

8. The process according to claim 1, the vitamin E product being non-toxic.

9. The process according to claim 1, the amla plant matter comprising a fruit derived from an amla tree.

10. The process according to claim 1, at least one converting step producing one of an annatto plant matter pulp and an amla plant matter pulp.

11. The process according to claim 1, further comprising extracting the spent plant matter from at least one previously conducted process according to claim 1 with one of water and dilute aqueous plant extract at a predetermined temperature and for a predetermined period of time.

12. The process according to claim 1, the annatto plant matter comprising at least one of leaves, fruit, flowers, stems, bark, seeds, roots, rhizomes and mixtures thereof.

13. The process according to claim 1, the amla plant matter comprising at least one of leaves, fruit, flowers, stems, bark, seeds, roots, rhizomes and mixtures thereof.

14. The process according to claim 1, either or both of the annatto and amla plant matters being treated prior to the respective converting steps by at least one of crushing, grinding, screening, mixing, drying, milling, homogenizing, washing, cleaning, blanching and a combination thereof.

15. The process according to claim 1, further comprising filtration of the first extract prior to the step of concentrating the first extract.

16. The process according to claim 1, the mixing step further comprising at least one of heating, stifling, agitating, cooking and combinations thereof.

17. The process according to claim 1, at least one of the mixing step and the extracting step further comprising the use of pressure.

18. The process according to claim 1, the process being operated continuously.

19. The process according to claim 1, the process being operated as a batch process.

20. The process according to claim 1, further comprising subjecting the vitamin E product to at least one of crushing, grinding, milling, screening, sifting, mixing, blending, homogenizing, agglomerating, pelletising, tableting and combinations thereof.

21. The process according to claim 1, the vitamin E product being one of a solid and a semi-solid.

22. The process according to claim 1, the annatto plant matter comprising annatto seeds and the amla plant matter comprising fruit matter.

23. The process according to claim 1, the extracting step including at least one of co-current extraction and counter-current extraction.

24. The process according to claim 1, the concentrating step being effected using at least one falling film evaporator.

25. A process for extracting vitamin E from annatto plant matter, the process comprising the steps of:
   providing annatto plant matter;
   converting the plant matter of the providing annatto step into a form having increased contact area;
   providing amla plant matter;
   converting the plant matter of the providing amla step into a form having increased contact area;
   producing a mixture that is more acidic than the annatto plant matter by mixing the annatto form having increased contact area with the amla form having increased contact area;
   extracting the mixture formed in the mixing step with one of water and dilute aqueous plant extract at a predetermined temperature and for a predetermined period of time to obtain a first extract and spent plant matter, the dilute aqueous extract used in the extracting step being a first extract from at least one previously conducted extracting process;
   concentrating the first extract to a semi-solid consistency; and
   adsorbing the concentrated first extract onto a solid excipient to form a second extract.

26. The process according to claim 25, further comprising the step of further drying the second extract.

27. A process for extracting vitamin E from annatto plant matter, the process comprising the steps of:
providing annatto plant matter;
converting the plant matter of the providing annatto step into a form having increased contact area;
providing a second plant matter comprising at least one acidic component;
converting the second plant matter into a form having increased contact area;
producing a mixture that is more acidic than the annatto plant matter by mixing the annatto form having increased contact area with the second plant matter form having increased contact area;
extracting the mixture formed in the mixing step with one of water and dilute aqueous plant extract at a predetermined temperature and for a predetermined period of time to obtain a first extract and spent plant matter, the dilute aqueous extract used in the extracting step being a first extract from at least one previously conducted extracting process;
concentrating the first extract; and
drying the first extract to yield a vitamin E product,
water or the first extract being the sole solvent utilized in the extraction process.

28. The process according to claim 27, the acidic component comprising at least one of citric acid, tartaric acid, ascorbic acid and succinic acid.

29. The process according to claim 27, the acidic component comprising at least one of citric acid, tartaric acid, ascorbic acid, succinic acid, cinnamic acid, ascorbic acid, folic acid, oxalic acid, hydroxycitric acid, rosmarinic acid, oleic acid, linoleic acid, palmitic acid, ursolic acid, stearic acid, chlorogenic acid and corosolic acid.

30. The process according to claim 27, the second plant matter comprising at least one of tamarind fruits (*Tamarindus indica*), guava fruits (*Psidum gujava*), lemon peels (*Citrus limon*), *Hibiscus subdarifa, Hibiscus rosasinensis, Garcinia cambogia, Garcinia indica*, rosemary leaves (*Rosmarinus officinalis*), acerola fruits (*Malpighia emarginata*), orange (*Citrus sinensis*), acai berries (*Euterpe oleracea*), holy basil leaves (*Ocimum sanctum*), banaba (*Lagerstroemia speciosa*), *Ziziphus jujube, Ziziphus spinosa* and *Ziziphus zizyphus*.

* * * * *